United States Patent
Cunningham

(10) Patent No.: US 7,121,519 B2
(45) Date of Patent: Oct. 17, 2006

(54) SILICONE MOULD TOOL

(75) Inventor: Chris Cunningham, Buckinghamshire (GB)

(73) Assignee: PerkinElmer International C.V., (CH)

( * ) Notice: Subject to any disclaimer, the term of this patent is extended or adjusted under 35 U.S.C. 154(b) by 310 days.

(21) Appl. No.: 10/438,125

(22) Filed: May 14, 2003

(65) Prior Publication Data

US 2004/0028563 A1 Feb. 12, 2004

(30) Foreign Application Priority Data

May 14, 2002 (EP) .................................. 02253344

(51) Int. Cl.
*B29C 39/26* (2006.01)
*B29C 33/38* (2006.01)

(52) U.S. Cl. ...................... 249/134; 249/140; 249/142; 249/177

(58) Field of Classification Search ................ 249/134, 249/127, 136, 140, 141, 142, 177, 57; 425/125
See application file for complete search history.

(56) References Cited

U.S. PATENT DOCUMENTS 3,815,863 A * 6/1974 Andeweg ................... 249/178
4,027,845 A * 6/1977 Putzer ........................ 249/142
4,076,791 A * 2/1978 Barter et al. ........... 264/272.15
4,986,965 A   1/1991 Ushikubo
5,814,695 A * 9/1998 Fitzgerald et al. .......... 524/731
5,938,993 A * 8/1999 Greene ...................... 264/46.4

FOREIGN PATENT DOCUMENTS

| EP | 0 767 369 A2 | 4/1997 |
| EP | 0 896 215 A1 | 2/1999 |
| GB | 414789 | 8/1934 |

OTHER PUBLICATIONS

European Search Report and Abstract for EP 02253344.2, Oct. 23, 2002, 4 pp.

* cited by examiner

*Primary Examiner*—Donald Heckenberg
(74) *Attorney, Agent, or Firm*—St. Onge Steward Johnston & Reens LLC

(57) ABSTRACT

A tool for making a mounting or holder for a tablet-shaped sample which is to undergo analysis in an analytical instrument, the tool comprising a moulding which defines a lower surface and a side wall or walls, and a pin which, in use, extends upwardly above the lower surface of the moulding. The arrangement being such that in use a tablet is mounted on the upper end of the pin and mouldable material is introduced into the moulding so that it locates around the lower part of the tablet.

6 Claims, 2 Drawing Sheets

SILICONE MOULD TOOL

This application claims priority of pending European Application No. 02253344.2 filed on May 14, 2002.

FIELD OF THE INVENTION

The present invention relates to a tool assembly which can be used to make a mounting or holder for a tablet-shaped sample which is to undergo analysis.

Analytical instruments such as FT-IR spectrometers are used to analyze samples. One type of sample which requires analysis in such an instrument is a tablet-shaped sample. Many pharmaceutical products are sold in the form of tablets. The manufacturers of such tablets are required to test those tablets in order to ensure that they meet the required specifications for content and concentration. One known way of testing such a tablet is to grind the tablet into a powder, dissolve it in a liquid and then analyze the resulting solution. More recently, systems have been developed which enable the tablet to be analyzed intact. In such a system a tablet is typically held in a V-shaped device by means of spring pressure and then located in an analytical instrument such as an FT-IR spectrometer for analysis in a known way. This procedure works well for round tablets, but is not satisfactory for irregularly shaped tablets and furthermore it is not always possible with such an arrangement to hold a series of tablets in a consistent and reproducible way.

It is also known to provide a holder machined out of metal which can receive a sample for analysis. However, the holder can only receive a tablet of a particular shape and if different shaped tablets are to be analyzed then a new holder needs to be obtained.

The present invention is concerned with a tool assembly which obviates all the abovementioned problems and enables a user of an analytical instrument to make their own holders or to have them made more cheaply.

According to the present invention there is provided a tool for making a mounting or holder for a tablet-shaped sample which is to undergo analysis in an analytical instrument, said tool comprising a moulding which defines a lower surface and a side wall or walls, and a pin which, in use, extends upwardly above the lower surface of the moulding, the arrangement being such that in use a tablet is mounted on the upper end of the pin and mouldable material is introduced into the moulding so that it locates around the lower part of the tablet.

After the mouldable material has set, a mounting or holder results which has a recess in its upper surface that matches the shape of the tablet and can therefore be used to support similar tablets in an analytical instrument such an FT-JR spectrometer.

The tool may comprise a base and a moulding. The pin may locate through a hole in the base member and a hole in the lower wall of the moulding. The moulding may be formed from silicone. The mouldable material be may be loaded resin such as loaded polyurethane. According to another aspect of the present invention, there is provided a method of making a mounting or holder for a tablet-shaped sample using a tool as defined above, said method comprising, securing a tablet to the upper end of the pin, introducing mouldable material into the moulding until it locates around a lower surface of the tablet, and allowing the mouldable material to solidify or set.

BRIEF DESCRIPTION OF DRAWINGS

The invention will be described by way of example only, with particular reference to the accompanying drawings. In the drawings.

DETAILED DESCRIPTION OF DRAWINGS

Figure 1:
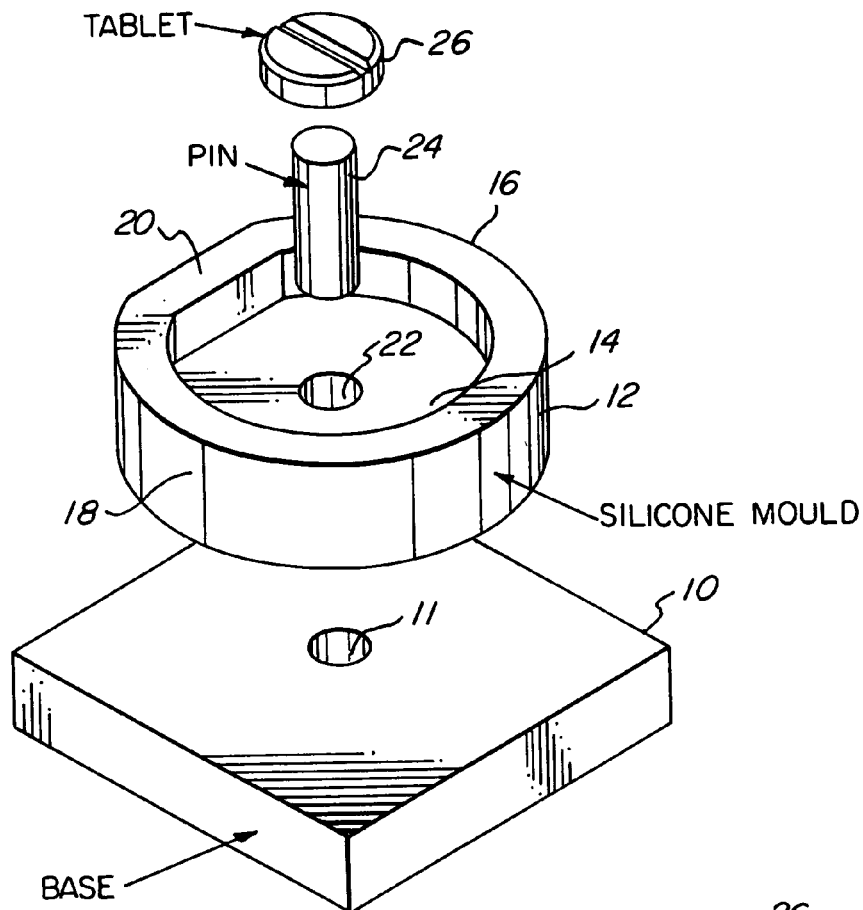
FIG. 1 is a perspective view showing a tool assembly in accordance with the present invention.

Referring to the drawings, a tool assembly comprises a base element (10). The base element (10) is generally square-shaped and can be made from any suitable rigid material. The base element (10) has a central through hole (11).

The tool assembly also includes a moulding (12). The moulding (12) is formed from silicone. The moulding (12) has a lower wall (14) and an upstanding side wall (16). The upstanding side wall is part circular as shown at (18) and part linear as shown at (20). The lower wall (14) of the moulding has a central through aperture (22), the diameter of which is substantially the same as that of the hole (11) in the base.

The tool assembly also includes a pin (24) whose radial dimensions are such that it can locate snugly within the hole (22) and the hole (11).

Figure 2A:
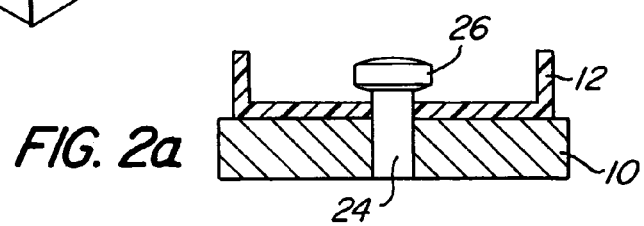
FIGS. 2a to 2c illustrate the steps which are carried out in order to form a mounting or holder.
Figure 2B:
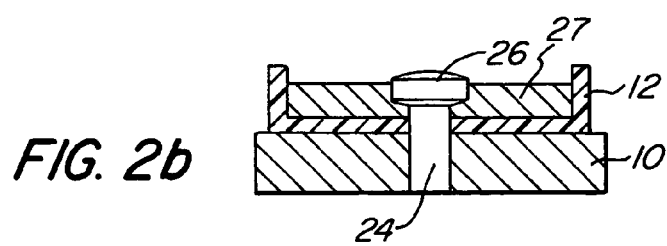

In use, a tablet (26) for which a holder or mounting is to be produced, is secured to the upper end of the pin (24) by means of a suitable adhesive, such as Superglue. The tablet is then painted with a suitable release agent. The pin/tablet assembly is then pushed into the silicone mould so that the pin (24) protrudes from the underside of the moulding into the base (10) as shown in FIG. 2a of the drawings. The assembly is then placed upon a flat surface with the lower end of the pin resting on the surface. Then mouldable material (27), such as loaded polyurethane, is introduced into the moulding (12), as shown in FIG. 2b of the drawings. The mouldable material is introduced until as shown in FIG. 2b it covers slightly more than half of the surface of the tablet (26). As an alternative to the abovementioned procedure, the initial step may comprise locating the pin and tablet assembly only partly into the hole in the base (10), introducing the mouldable material into the moulding (12) and then pushing the pin-tablet assembly into the base element (10) until the lower end of the pin (24) locates against the flat surface as shown in FIG. 2b of the drawings.

After the above steps have been carried out, the mouldable material is then allowed to cure, following which the tablet-pin assembly is pushed up and out of the base and moulding. This will be assisted by the fact that the tablet had previously been coated with a release agent. The completed holder can then be removed from the silicone mould.

Figure 2C:
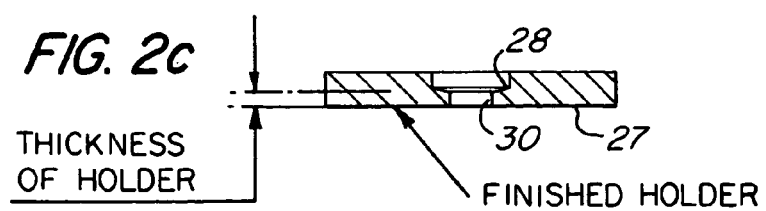
Figure 3:
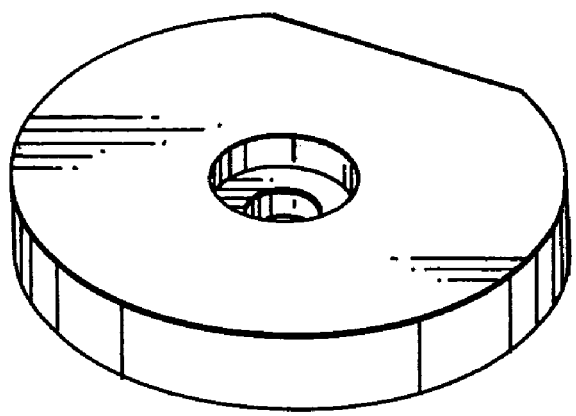
FIG. 3 is a perspective view of a completed moulding.

As shown in FIG. 2c, the holder (27) has a depression or recess (28) which matches the shape of the tablet used to produce it. Therefore other tablets of the same shape and dimension can be located precisely in the recess. Additionally, the holder has a hole (30) which allows the tablet to be exposed to an analyzing beam when placed in the analytical instrument. The structure of the holder (27) is such that radiation from the analyzing beam, when the holder is in the instrument, is prevented from leaking around the side of the tablet, because of the fact that the holder is an excellent fit around the tablet and the hole size (30), which allows the analyzing radiation to impinge upon the tablet, is significantly smaller than the tablet being tested.

It will be appreciated that in forming the holder (27) the height of the tablet from the bottom of the holder is in effect controlled by appropriately selecting the length of the pin (24) and the thickness of the base and the thickness of the silicone moulding.

It will be appreciated that the tool assembly described above can be used by an operator of an analytical instrument such as an FT-IR spectrometer in order to produce holders for a wide range of tablet size and shapes. The user of such an instrument can in a very simple manner make their own tablet holders and such holders can be made accurately and in such a way as to ensure that the tablets can be located successively into an analytical instrument in a reproducible manner.

Figure 4:
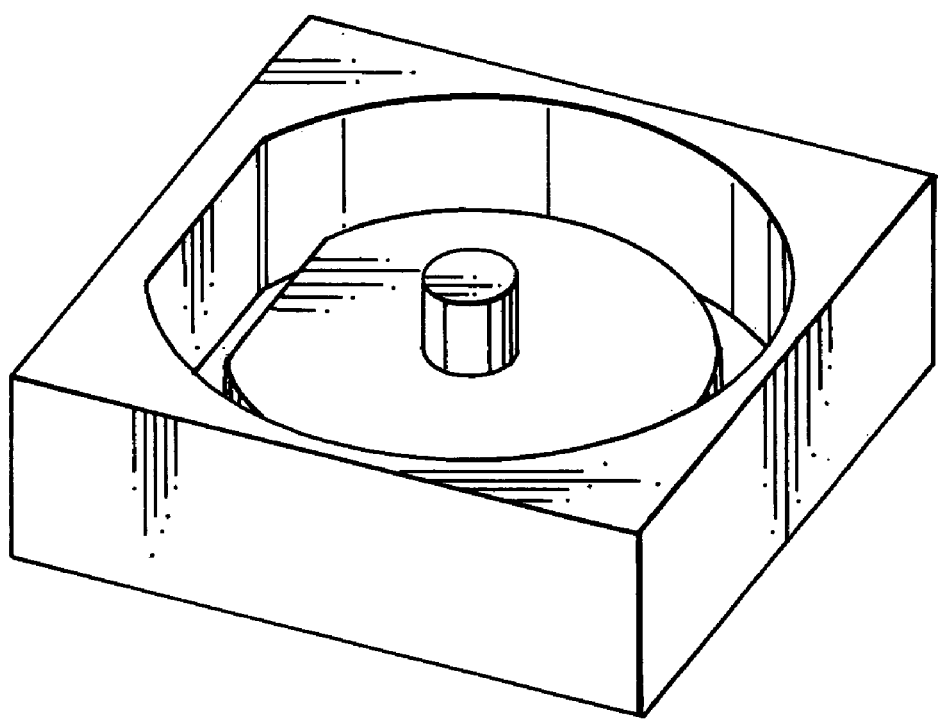
FIG. 4 shows a tool which can be used to make a silicone mould.

FIG. 4 is a view of tool which can be used to make the silicone moulding (12).

The invention claimed is:

1. A system for making a mounting or holder for a tablet-shaped sample which is to undergo analysis in an analytical instrument, said system comprising:
   (a) a moulding which defines a lower surface and a side wall or walls, said moulding having a hole that extends through it and said moulding being open opposite the lower surface it defines;
   (b) a pin which extends upwardly above the lower surface defined by the moulding and through the hole in the moulding;
   (c) a tablet having a lower surface and a side surface;
   (d) a mould cavity defined by said moulding, pin and tablet; and
   (e) a material that at a first point in time is mouldable and at a second point in time is substantially less mouldable, said material filling the mould cavity only up to a level along the side surface of said tablet and above the lower surface of said tablet, said material defining a mounting or holder when said material is substantially less mouldable.

2. A system according to claim 1, further comprising a base member.

3. A system according to claim 2 wherein the pin locates through a hole in the base member.

4. A system according to claim 1 wherein the moulding is formed from silicone.

5. A system according to claim 1 wherein said material is a loaded resin.

6. A system according to claim 5 wherein the loaded resin is loaded polyurethane.

* * * * *